US009267940B2

United States Patent
Iwamoto et al.

(10) Patent No.: US 9,267,940 B2
(45) Date of Patent: Feb. 23, 2016

(54) DISC-LIKE ASSAY CHIP

(71) Applicant: Rohm Co., Ltd., Kyoto (JP)

(72) Inventors: Keiji Iwamoto, Kyoto (JP); Kazuhiro Oguchi, Kyoto (JP); Kenji Hamachi, Kyoto (JP)

(73) Assignee: Rohm Co., Ltd., Kyoto (JP)

( * ) Notice: Subject to any disclaimer, the term of this patent is extended or adjusted under 35 U.S.C. 154(b) by 0 days.

(21) Appl. No.: 14/642,860

(22) Filed: Mar. 10, 2015

(65) Prior Publication Data

US 2015/0226730 A1 Aug. 13, 2015

Related U.S. Application Data

(62) Division of application No. 13/428,683, filed on Mar. 23, 2012, now Pat. No. 9,005,547.

(30) Foreign Application Priority Data

Mar. 23, 2011 (JP) ................... 2011-064490
Apr. 1, 2011 (JP) ................... 2011-081979

(51) Int. Cl.
*B01L 3/00* (2006.01)
*G01N 33/53* (2006.01)
*G01N 21/07* (2006.01)
*G01N 35/00* (2006.01)
*G01N 21/64* (2006.01)

(52) U.S. Cl.
CPC .......... *G01N 33/5302* (2013.01); *B01L 3/5085* (2013.01); *B01L 3/502723* (2013.01); *B01L 3/502738* (2013.01); *G01N 21/07* (2013.01); *G01N 35/00069* (2013.01); *B01L 2200/0605* (2013.01); *B01L 2200/0621* (2013.01); *B01L 2200/10* (2013.01); *B01L 2300/0803* (2013.01); *B01L 2300/087* (2013.01); *B01L 2300/0864* (2013.01); *B01L 2300/0867* (2013.01); *B01L 2400/0409* (2013.01); *G01N 21/6428* (2013.01)

(58) Field of Classification Search
CPC ........... B01L 2400/0409; G01N 21/07; G01N 2035/00495
USPC ..................................... 422/503, 72
See application file for complete search history.

(56) References Cited

U.S. PATENT DOCUMENTS

2004/0120856 A1 6/2004 Andersson et al.
2008/0193336 A1* 8/2008 Cho et al. ................. 422/100

FOREIGN PATENT DOCUMENTS

EP 1994987 A2 11/2008

OTHER PUBLICATIONS

Hizuru Nakajima, "Flow Analysis Method Using a Compact Disk-Like Abstract Only Microchip," The Japan Society for Analytical Chemistry, pp. 381-382 (Jul. 2009).

*Primary Examiner* — Natalia Levkovich
(74) *Attorney, Agent, or Firm* — Fish & Richardson P.C.

(57) ABSTRACT

The present invention provides a disc-like assay chip, and more specifically, the present invention provides an assay chip which can effectively clean a cleaned object existing in a fluid loop, and can be appropriately applied to a detection method of a reaction system using a step of necessarily cleaning the cleaned object, such as an immunofluorescent antibody method, and applied to a detection method using an enzymatic reaction (especially, an ELISA method). The present invention further provides a disc-like assay chip which is mounted on a centrifugal device such as a rotational disc and can perform detection or quantitation on a target substance through optical measurement after a specimen and a reagent react by use of a centrifugal force generated by rotation of the centrifugal device.

22 Claims, 7 Drawing Sheets

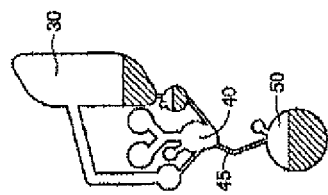
FIG 4E
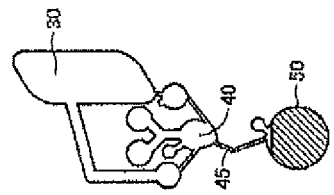
FIG 4J
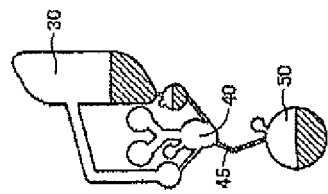
FIG 4D
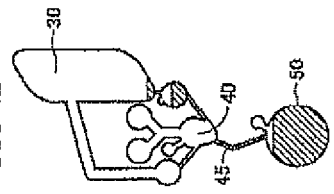
FIG 4I
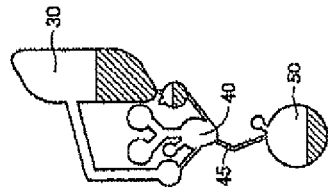
FIG 4C
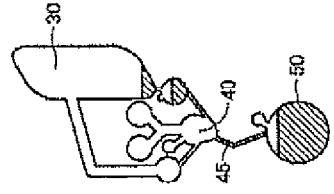
FIG 4H
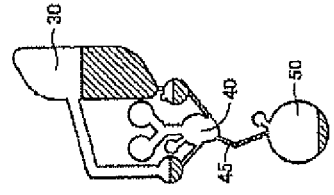
FIG 4B
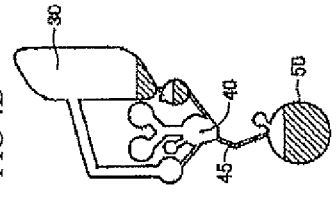
FIG 4G
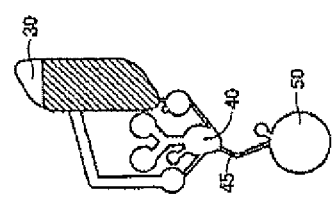
FIG 4A
FIG 4F

DISC-LIKE ASSAY CHIP

CROSS-REFERENCE TO RELATED APPLICATIONS

This application is a divisional of U.S. patent application Ser. No. 13/428,683 filed Mar. 23, 2012, which claims the benefit of priority from Japanese Patent Application Nos. 2011-064490, filed on Mar. 23, 2011 and 2011-081979, filed on Apr. 1, 2011, the entire contents of which are incorporated herein by reference.

BACKGROUND OF THE INVENTION

1. Field of the Invention

The present invention relates to an assay chip which can be appropriately used in various biochemical detections, and more specifically, the present invention relates to a disc-like assay chip which is mounted on a centrifugal device such as a rotational disc and can perform detection or quantitation on a target substance through optical measurement after a specimen and a reagent react by use of a centrifugal force generated by rotation of the centrifugal device.

2. Description of the Related Art

Recent developments in the fields of medical treatment, healthcare, food, and medicine have heightened the importance of probing, detecting or quantifying biological substances and chemical substances such as Deoxyribo Nucleic Acid (DNA) or enzyme, antigen, antibody, protein, virus and cell. To address this issue, the invention proposes various assay chips and miniature chemical chips (hereinafter collectively referred to as assay chips) which provide simple and convenient measurement of these substances. A series of assay and experiment operations performed in a laboratory can be performed on a miniature chip within a chip. Such a chip has numerous advantages: only a small quantity of specimens and reagents are required, the detection can be performed at low cost, high speed, and with high yield, and the detection results can be immediately obtained at the site where the specimens are collected. This assay chip is appropriate for use in biochemical detection such as blood detection.

The prior art includes examples of an assay chip formed on a disc-like substrate like an optical disk and having multiple liquid storage grooves (grooves) and minute flow paths for connecting these grooves (hereinafter, the whole loop (pattern) including various liquid storage grooves and flow paths for connecting these grooves of the assay chip formed on the substrate is collectively referred to as a fluid loop), and a centrifugal force generated by rotation of the disc whose center serves as the centrifugal center is used to move liquids (specimens or reagents) in the liquid storage grooves, thereby performing the specified reaction (such as in non-patent document 1). This disc-like assay chip also has many of the advantages described above; then, centrifugal force is used, so peripheral apparatuses such as a pump or valve are not required. The disc-like assay chip also has substantial advantage in that it enables miniaturization of the whole assay system.

Non-patent document 1: Hizuru Nakajima, "FLOW ANALYSIS METHOD USING A COMPACT DISK-LIKE MICROCHIP," The Japan Society for Analytical Chemistry, July 2009, p. 381-382

SUMMARY OF THE INVENTION

The assay chip is intended to implement various detection and assay methods (applied to different types of reaction systems), including the immunofluorescent antibody method generally used in biochemical detection. The so-called immunofluorescent antibody method is one of various methods for quantitatively detecting a small quantity of target substances included in specimens (samples) (detecting substances of an object) by use of an antigen antibody reaction. For example, 1) a specimen (sample) containing a target substance, 2) a solid phase of a particle decorated with an antibody specifically combined with the target substance, and 3) an antibody specifically combined with a combination of the target substance and the particle decorated with an antibody, and an antibody identified with a fluorescent substance (below, called a fluorescent identification antibody), 1) to 3) are mixed to perform the antigen antibody reaction; after the unreacted specimen (the ingredient substituted for the target substance) and the unreacted fluorescent identification antibody are cleaned and removed, fluorescent measurement is implemented on the combination of the target substance, the particle decorated with the antibody and the fluorescent identification antibody, so that the target substance can be quantified according to fluorescence intensity.

The detection method of the reaction system requires cleaning and removal of the unreacted substance (such as, an Enzyme-Linked Immunosorbent Assay (ELISA) method using an enzyme identification antibody), such as the immunofluorescent antibody method, in order to ensure reliably accurate quantitation of the target substance and the measurement reliability, the unreacted substance must be prudently cleaned and removed. For example, if the unreacted (episomal) fluorescent identification antibody remains, a significant measurement error will result in the immunofluorescent antibody method.

The assay chip which is invented by the present inventor et al. and is capable of removing the unreacted substance via washing can be illustrated as an assay chip having a fluid loop shown in FIG. 1. The fluid loop shown in FIG. 1 is formed into a groove pattern on a disc-like substrate, and includes: a first groove 1, for accommodating a sample liquid containing a target substance and a fluorescent identification antibody; a second groove 2, for accommodating a liquid containing a particle decorated with the antibody (antibody decorated particle); a third groove 3, for accommodating a cleaning fluid; a fourth groove 4, disposed at a side closer to a peripheral portion of the assay chip than the first groove 1, the second groove 2 and the third groove 3 (a side downstream of the centrifugal force direction), and mixing the sample liquid, the fluorescent identification antibody and the antibody decorated particle to perform an antigen antibody reaction; a fifth groove 5 (in the groove, connecting an air hole 5a through a flow path), disposed at a side closer to the peripheral portion of the assay chip than the fourth groove 4 (a side downstream of the centrifugal force direction), and accommodating a waste liquid; a first flow path 6, for connecting the first groove 1 and the fourth groove 4; a second flow path 7, connected to the first flow path 6, and connecting the second groove 2 and the fourth groove 4; a third flow path 8, for connecting the third groove 3 and the fourth groove 4; and a fourth flow path 9, for connecting the fourth groove 4 and the fifth groove 5. The cross-sectional areas of the first flow path to the fourth flow path are designed in a manner such that the first flow path 6=the second flow path 7>the fourth flow path 9>the third flow path 8. Additionally, the cross-sectional area of the fourth flow path 9 is less than the size of the antibody decorated particle.

Moreover, in order to prevent the liquid in the fluid loop from leaking, stacking members such as a substrate covering the fluid loop or a binding seal strip are stacked on a disc-like substrate formed with the groove pattern (fluid loop). An injection portion for injecting the sample liquid and the fluorescent identification antibody, and an injection portion for injecting the liquid containing the antibody decorated particle are disposed in the stacking member. These injection portions are penetrating openings penetrating along the thickness direction. Additionally, the air hole 5a is formed with a groove formed on the disc-like substrate and a penetrating opening formed on the stacking member stacked on the disc-like substrate and communicated with the groove. According to the assay chip having the fluid loop shown in FIG. 1, the detection through the immunofluorescent antibody method can be implemented in the following sequence by use of centrifugal force. First, the sample liquid containing the target substance and the fluorescent identification antibody are injected in the first groove 1, the liquid containing the antibody decorated particle is injected in the second groove 2, and the cleaning fluid is injected in the third groove 3 (step 1). Next, through the rotation of the assay chip whose center serves as the rotation center, a first centrifugal force in the direction shown in the drawing is applied to the assay chip (a centrifugal force which prevents the cleaning fluid from being discharged from the third groove 3), so the sample liquid containing the target substance, the fluorescent identification antibody and the liquid containing the antibody decorated particle are guided into the fourth groove 4 and these substances are mixed to perform the antigen antibody reaction (step 2).

Then, a second centrifugal force (which is greater than the first centrifugal force) is applied in the direction shown in the drawing, so that the liquid is moved from the fourth groove 4 to the fifth groove 5, thereby moving the waste liquid (step 3). Next, a third centrifugal force (which is greater than the second centrifugal force) is applied in the direction shown in the drawing, the cleaning fluid in the third groove 3 is guided into the fourth groove 4 to clean the combination of the target substance, the antibody decorated particle and the fluorescent identification antibody, and the cleaning fluid is moved to the fifth groove 5 after the cleaning (step 4). Through step 4, the unreacted sample and the unreacted fluorescent identification antibody are removed. Finally, the detection light is irradiated on the combination of the target substance, the antibody decorated particle and the fluorescent identification antibody accommodated in the fourth groove 4 to perform fluorescent measurement, thereby quantifying the target substance (step 5).

As described above, according to the assay chip having the fluid loop shown in FIG. 1, the cross-sectional areas of the first flow path to the fourth flow path are set to an appropriate size, and these flow paths are endowed with valve functions to different extents (capability for restraining the liquid discharge), so the desired liquid can be moved at a desired time point, and therefore, a unidirectional centrifugal force can be applied to perform the following successive operations, that is, after performing the antigen antibody reaction, the liquid is discharged, and then the cleaning fluid is guided to perform cleaning.

However, for the assay chip having the fluid loop shown in FIG. 1, there is still room for improving the cleaning effect of the cleaning fluid. That is to say, in the case of the fluid loop shown in FIG. 1, the cleaning in step 4 can only be performed once (that is to say, in step 4, the centrifugal force is applied to guide all of the cleaning fluid in the third groove 3 into the fourth groove 4); further research by the present inventor et al. found that performing the cleaning only once a fully clean cannot be made, and some of the unreacted substance remains in the fourth groove 4 after the cleaning. Additionally, if an excessive amount of the cleaning fluid is accommodated in the third groove 3, the third flow path 8 cannot fully bring out the valve function in itself, and the centrifugal force applied in step 3 can produce unintentional discharge of the cleaning fluid.

An objective of the present invention lies in providing an assay chip which can effectively clean an object to be cleaned existing in the fluid loop, and can be appropriately applied to a detection method of a reaction system using a step of cleaning the object to be cleaned, such as the immunofluorescent antibody method.

Additionally, the assay chip which is intended to implement various detection and assay methods (applied to different types of reaction systems) can be illustrated as the Enzyme-Linked Immunosorbent Assay (ELISA) method generally used in the biochemical detection. The so-called ELISA method is one of the methods that commonly employed for quantitatively detecting a small quantity of target substances included in specimens (samples) (detecting substances of an object) by use of an enzymatic reaction, and has beneficial characteristics of detecting the target substance with high sensitivity, and enables excellent quantitation.

In the ELISA method, for example, 1) a specimen (sample) containing a target substance, 2) a solid phase of a particle decorated with an antibody specifically combined with the target substance, and 3) an antibody specifically combined with a combination of the target substance and the particle decorated with an antibody, and an antibody identified with an enzyme (below, called an enzyme identification antibody), 1) to 3) are mixed to perform the antigen antibody reaction; after the unreacted specimen (the ingredient instead of the target substance) and the unreacted enzyme identification antibody are cleaned and removed, an enzymatic reaction is performed between them and the matrix solution, and the generated fluorescent substance is detected so that the target substance can be quantified.

In the procedure of developing a disc-like assay chip on which the ELISA method can be appropriately implemented, the present inventor et al. created the assay chip having a fluid loop shown in FIG. 6. The fluid loop shown in FIG. 6 is formed as a groove pattern on a disc-like substrate, and includes: a first groove 1, for accommodating a sample liquid containing a target substance and an enzyme identification antibody; a second groove 2, for accommodating a liquid containing a particle decorated with the antibody (antibody decorated particle); a third groove 3, for accommodating a cleaning fluid; a fourth groove 4, for accommodating a matrix solution; a fifth groove 5, disposed at a side closer to a peripheral portion of the assay chip than the first groove 1, the second groove 2, the third groove 3 and the fourth groove 4 (a side downstream of the centrifugal force direction), and mixing the sample liquid, the enzyme identification antibody and the antibody decorated particle to perform an antigen antibody reaction, and to perform an enzymatic reaction with the matrix solution; a sixth groove 6 (in the groove, connecting an air hole 6a through a flow path), disposed at a side closer to the peripheral portion of the assay chip than the fifth groove 5 (a side downstream of the centrifugal force direction), and accommodating a waste liquid; a first flow path 7, for connecting the first groove 1 and the fifth groove 5; a second flow path 8, connected to the first flow path 7, and connecting the second groove 2 and the fifth groove 5; a third flow path 9, for connecting the third groove 3 and the fifth groove 5; a fourth flow path 10, for connecting the fourth groove 4 and the fifth groove 5; and a fifth flow path 11, for connecting the fifth groove 5 and the sixth groove 6.

The cross-sectional areas of the first flow path to the fifth flow path are designed in a manner such that the first flow path 7=(or ≈) the second flow path 8>the fifth flow path 11>the third flow path 9>the fourth flow path 10. Additionally, the cross-sectional area of the fifth flow path 11 is less than the size of the antibody decorated particle.

Moreover, in order to prevent the liquid in the fluid loop from leaking, stacking members such as a substrate covering the fluid loop or a binding seal strip are stacked on a disc-like substrate formed with the groove pattern (fluid loop). An injection portion for injecting the sample liquid and the enzyme identification antibody, an injection portion for injecting the liquid containing the antibody decorated particle, and an injection portion for injecting the matrix solution are disposed in the stacking member. These injection portions are penetrating openings penetrating the stacking member along the thickness direction. Additionally, the air hole 6a is a hole enabling the fluid loop to be in communication with the exterior of the assay chip, and is formed with a groove formed on the disc-like substrate and a penetrating opening formed on the stacking member stacked on the disc-like substrate and communicated with the groove.

According to the assay chip having the fluid loop shown in FIG. 6, the detection through the ELISA method can be implemented in the following sequence by use of centrifugal force.

First, the sample liquid containing the target substance and the enzyme identification antibody are injected in the first groove 1, the liquid containing the antibody decorated particle is injected in the second groove 2, the cleaning fluid is injected in the third groove 3, and the matrix solution is injected in the fourth groove 4 (step 1). Next, through the rotation of the assay chip whose center serves as the rotation center, a first centrifugal force in the direction shown in the drawing is applied to the assay chip (a centrifugal force which prevents the cleaning fluid from being discharged from the third groove 3 and prevents the matrix solution from being discharged from the fourth groove 4), so the sample liquid containing the target substance, the enzyme identification antibody and the liquid containing the antibody decorated particle are guided into the fifth groove 5 and these substances are mixed to perform the antigen antibody reaction (step 2).

Then, a second centrifugal force (which is greater than the first centrifugal force) is applied in the direction shown in the drawing, so that the liquid is moved from the fifth groove 5 to the sixth groove 6, thereby moving the waste liquid (step 3). Next, a third centrifugal force (which is greater than the second centrifugal force and sufficient to prevent the matrix solution from being discharged from the fourth groove 4) is applied in the direction shown in the drawing, the cleaning fluid in the third groove 3 is guided into the fifth groove 5 to clean the combination of the target substance, the antibody decorated particle and the enzyme identification antibody, and the cleaning fluid is moved to the sixth groove 6 after the cleaning (step 4). The unreacted sample and the unreacted enzyme identification antibody are thus removed in step 4.

Next, a fourth centrifugal force (which is greater than the third centrifugal force) is applied in the direction shown in the drawing, and the matrix solution in the fourth groove 4 is guided into the fifth groove 5 to perform the enzymatic reaction (step 5). The matrix solution guided into the fifth groove 5 through the centrifugal force is moved to the sixth groove 6. Finally, the fluorescent substance generated in the fifth groove 5 is detected through the enzymatic reaction (the detection light is irradiated on the fifth groove 5), thereby quantifying the target substance (step 6).

As described above, according to the assay chip having the fluid loop shown in FIG. 6, the cross-sectional areas of the first flow path to the fifth flow path are set to an appropriate size, and these flow paths are endowed with valve functions to different extents (capability for restraining the liquid discharge), so the desired liquid can be moved at a desired time point, and therefore, a unidirectional centrifugal force can be applied to perform the following successive operations, that is, after performing the antigen antibody reaction, the liquid is discharged; then the cleaning fluid is guided to perform cleaning; afterwards the enzymatic reaction is performed.

However, in the assay chip having the fluid loop shown in FIG. 6, the enzymatic reaction step via the matrix solution still needs to be improved further. That is to say, in order for the steps to proceed in proper succession, the cross-sectional area of the fifth flow path 11 must be greater than the cross-sectional area of the fourth flow path 10, so that when the centrifugal force is applied in step 5, the matrix solution guided into the fifth groove 5 will not remain deposited in the fifth groove 5, but flow into the sixth groove 6, so that the enzymatic reaction can be fully performed.

Another objective of the present invention lies in providing an assay chip which can be appropriately applied to a detection method using the enzymatic reaction (especially, the ELISA method).

In order to achieve this objective, the inventor et al. performed diligent research and discovered that increasing the flowing time of the cleaning fluid is extremely effective relative to increasing the quantity of cleaning fluid. Even if the same quantity of cleaning fluid is used, the cleaning effect is significantly improved by repeated application. Further research led to the invention of the fluid loop constructed such that the cleaning fluid accommodated in a liquid storage groove (groove) can be discharged more than once, thereby improving the cleaning effect.

That is to say, the present invention provides a disc-like assay chip, which includes an internal space (fluid loop) to which a centrifugal force is applied to move a liquid existing in the internal space to a desired position in the internal space (fluid loop), in which the internal space (fluid loop) includes: a first groove, used for accommodating a first liquid; a second groove, used for accommodating a second liquid; a third groove, used for accommodating a third liquid; a fourth groove, disposed at a side closer to a peripheral portion of the assay chip than the first groove, the second groove and the third groove; a fifth groove, disposed at a side closer to the peripheral portion of the assay chip than the fourth groove; a first flow path, for connecting the first groove and the fourth groove; a second flow path, for connecting the second groove and the fourth groove; a third flow path, for connecting the third groove and the fourth groove; a fourth flow path, for connecting the fourth groove and the fifth groove; and a first buffering groove, configured on the third flow path, and having a first air hole in communication with an exterior of the assay chip; wherein the cross-sectional areas of the first flow path and the second flow path are greater than that of the fourth flow path, and the cross-sectional area of the fourth flow path is greater than that of the third flow path.

In the present invention, preferably, the internal space (the fluid loop) further includes a second buffering groove, and the second buffering groove is disposed at a side closer to the peripheral portion of the assay chip than the third groove, and closer to a central portion of the assay chip than the fourth groove. The second buffering groove and the first buffering groove are connected to third groove and the fourth groove through a flow path.

The fourth groove preferably has a second air hole in communication with the exterior of the assay chip. Additionally, the fifth groove preferably has a third air hole in communication with the exterior of the assay chip.

In the present invention, for example, the first liquid contains a sample as an assay object and an antibody identified with a fluorescent substance, the second liquid contains a particle decorated with an antibody, and the third liquid can be a cleaning fluid.

Additionally, another embodiment of the present invention relates to a disc-like assay chip which includes an internal space (fluid loop), and to which a centrifugal force is applied to move a liquid existing in the internal space to a desired position in the internal space. In the disc-like assay chip of the present invention, the internal space (the fluid loop) includes: a first groove, used for accommodating a first liquid; a second groove, used for accommodating a second liquid; a third groove, used for accommodating a third liquid; a fourth groove, used for accommodating a fourth liquid; a fifth groove, disposed at a side closer to a peripheral portion of the assay chip than the first groove, the second groove, the third groove and the fourth groove; a sixth groove, disposed at a side closer to the peripheral portion of the assay chip than the fifth groove; a first flow path, for connecting the first groove and the fifth groove; a second flow path, for connecting the second groove and the fifth groove; a third flow path, for connecting the third groove and the fifth groove; a fourth flow path, for connecting the fourth groove and the fifth groove; and a fifth flow path, for connecting the fifth groove and the sixth groove.

In the disc-like assay chip of the present invention, the cross-sectional areas of the first flow path and the second flow path are greater than that of the fifth flow path, the cross-sectional area of the fifth flow path is greater than that of the third flow path, and the cross-sectional area of the third flow path is greater than the cross-sectional area of the fourth flow path. Additionally, the total volume of the fifth flow path and the sixth groove is less than the total volume of the first liquid, the second liquid, the third liquid and the fourth liquid.

In the disc-like assay chip of the present invention, preferably, the internal space (the fluid loop) further includes a seventh groove disposed at a side closer to the peripheral portion of the assay chip than the fifth groove and connected to the fifth groove through a sixth flow path.

Additionally, in the disc-like assay chip of the present invention, preferably, the internal space (the fluid loop) further includes a first air hole, which is disposed at a side closer to a central portion of the assay chip than the sixth groove, is connected to the sixth groove through a seventh flow path, and is in communication with an exterior of the assay chip. In this case, preferably, the cross-sectional area of the fifth flow path and the cross-sectional area of the seventh flow path are substantially or entirely the same.

In the disc-like assay chip of the present invention, the internal space (the fluid loop) can further include a first buffering groove, which is configured on the third flow path and has a second air hole in communication with an exterior of the assay chip. Additionally, the internal space can further include a second buffering groove in which is disposed at a side closer to a central portion of the assay chip than the fifth groove and is connected to the third groove and the fifth groove through a flow path.

In another embodiment of the present invention, for example, the first liquid contains a sample as an assay object and an antibody identified with an enzyme, the second liquid contains a particle decorated with an antibody, the third liquid can be a cleaning fluid, and the fourth liquid can be a matrix solution.

Effects of the Invention

According to the disc-like assay chip of the present invention, the third liquid (the cleaning fluid) accommodated in the third groove can be guided into the fourth groove more than once, so the object to be cleaned existing in the fourth groove can be cleaned very effectively. The disc-like assay chip of the present invention can be appropriately applied to a detection method of a reaction system using a step of cleaning the object to be cleaned (more specifically, cleaning and removing the unreacted substance), such as the immunofluorescent antibody method.

Additionally, according to the disc-like assay chip of another embodiment of the present invention, in the step of guiding the matrix solution into the fifth groove, the matrix solution can be deposited in the fifth groove, so the enzymatic reaction via the matrix solution can be fully performed. In this way, improvement can be accomplished in precision of detection achieved by the ELISA method by use of the enzymatic reaction.

BRIEF DESCRIPTION OF THE DRAWINGS

FIG. 4 (a) to FIG. 4 (j) are schematic views showing experiment results of guiding water from a third groove into a fourth groove more than once by use of a disc-like assay chip of the present invention having the fluid loop shown in FIG. 3.

DETAILED DESCRIPTION OF THE INVENTION

Figure 2:
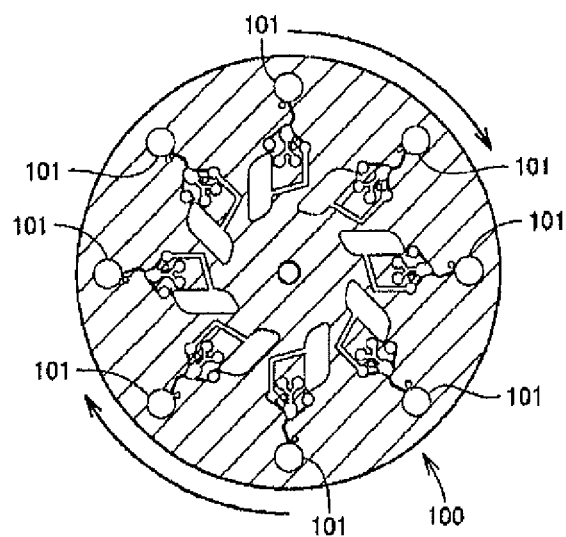
FIG. 2 is a schematic top view showing an example of a disc-like assay chip of the present invention.

FIG. 2 is a schematic top view showing an example of a disc-like assay chip of the present invention. The disc-like assay chip 100 shown in FIG. 2 has fluid loops 101 mainly including various grooves (liquid storage grooves) or minute flow paths connected to these grooves. A centrifugal force is provided by rotating the assay chip along the direction as shown in the drawing (or an opposite direction), and liquids (such as, a sample liquid, a reagent liquid, a cleaning fluid, and a waste liquid) in the fluid loop 101 can be moved to a desired position (location) in the fluid loop 101. In the example shown in FIG. 2, the disc-like assay chip 100 has eight fluid loops 101 of the same shape (pattern), and can simultaneously implement eight detections and assays in parallel. The eight fluid loops 101 are arranged along the radial direction of the disc (that is to say, the direction of the centrifugal force for rotating the assay chip with the center of the disc as the centrifugal center). Moreover, although in the example shown in FIG. 2, the number of fluid loops 101 is eight, the number of loops is not limited thereto, and can be less than or greater than eight.

The fluid loop 101 is a space formed in the disc-like assay chip 100. The disc-like assay chip having this fluid loop can be manufactured by forming a groove pattern corresponding to the constitution of the fluid loop on a disc-like first substrate, and stacking and bonding a second substrate on the groove forming face of the first substrate. The groove pattern forming the fluid loop can also be formed on the stacked second substrate. Additionally, the second substrate can also be replaced, and the disc-like assay chip can be manufactured by stacking other stacking members such as a binding seal strip on the groove forming face of the first substrate.

The substrate material forming the disc-like assay chip is not specially limited, and for example, Polymethyl Methacrylate (PMMA), Polydimethylsiloxane (PDMS), glass, Cyclo Olefin Polymer (COP), Cyclo Olefin Copolymer (COC), Polyethylene Terephthalate (PET), Polystyrene (PS), and Polypropylene (PP) can be listed. As far as the industrial production rate is concerned, it is appropriate to use PMMA, PET, COP, and COC. In a case of performing fluorescent measurement while assaying the disc-like assay chip, the substrate material preferably is a material which generates fluorescence difficultly. The material generating fluorescence difficultly preferably is methacrylic resin or cyclo olefin resin, and specifically PMMA, COP, and COC can be listed.

The thickness of the disc-like assay chip is not specially limited, and preferably is 0.1 to 100 mm, and more preferably is 2 to 3 mm. The method for forming a groove pattern on a substrate of the disc-like assay chip is not specially limited, and the mechanical process, the sandblast process, and the injection molding can be listed. As the method for bonding substrates with each other, a method for melting and welding a binding face of at least one substrate (welding method), and a method for performing adhering by using an adhesive can be listed. As the welding method, a method for heating and welding a substrate; a method for performing welding through heat generated during light absorption after a light such as laser light is irradiated (laser welding); and a method for performing welding by using an ultrasonic wave can be listed. Preferably, the laser welding method is used.

Figure 3:
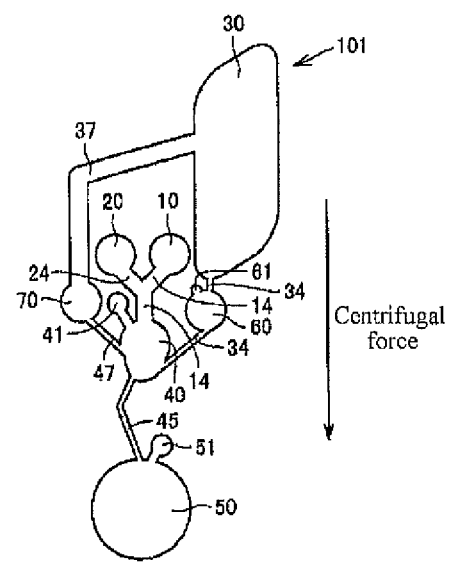
FIG. 3 is a schematic top view showing a preferable example of a constitution of a fluid loop of a disc-like assay chip of the present invention.

Next, the constitution of the fluid loop of the disc-like assay chip of the present invention is illustrated in detail by showing an embodiment. FIG. 3 is a schematic top view showing a preferable example of a constitution of a fluid loop of a disc-like assay chip of the present invention, and is an enlarged view showing the fluid loop 101 of the disc-like assay chip 100 shown in FIG. 2. The fluid loop 101 of the disc-like assay chip of the present embodiment has a constitution as follows, which can be appropriately applied to a detection method of a reaction system using a step of cleaning the object to be cleaned, such as the immunofluorescent antibody method or the ELISA method using an enzyme identification antibody.

As shown in FIG. 3, the fluid loop 101 mainly includes: a first groove 10, used for accommodating a first liquid; a second groove 20, used for accommodating a second liquid; a third groove 30, used for accommodating a third liquid; a fourth groove 40, disposed at a side (a side downstream of the centrifugal force direction) closer to a peripheral portion of the assay chip than the first groove 10, the second groove 20 and the third groove 30; a fifth groove 50, disposed at a side (a side downstream of the centrifugal force direction) closer to a peripheral portion of the assay chip than the fourth groove 40; a first flow path 14, for connecting the first groove 1 and the fourth groove 40; a second flow path 24, connected to the first flow path 14, and connecting the second groove 2 and the fourth groove 40; a third flow path 34, for connecting the third groove 30 and the fourth groove 40; a fourth flow path 45, for connecting the fourth groove 40 and the fifth groove 50; a first buffering groove 60, configured on the third flow path 34; a second buffering groove 70; a fifth flow path 37, for connecting the third groove 30 and the second buffering groove 70; and a sixth flow path 47, for connecting the fourth groove 40 and the second buffering groove 70.

For example, in a case where the disc-like assay chip of the present embodiment is used to perform detection through the immunofluorescent antibody method, the first liquid contains a sample including the target substance as an assay object and an antibody identified with a fluorescent substance (the fluorescent identification antibody), the second liquid contains a particle decorated with an antibody (the antibody decorated particle), and the third liquid can be a cleaning fluid. The particle size of the antibody decorated particle is not specially limited; for example, the commonly employed antibody decorated particle size of 75 μm can be used.

The first buffering groove 60, the fourth groove 40 and the fifth groove 50 respectively have the first air hole 61, the second air hole 41, and the third air hole 51 in communication with the exterior of the assay chip. These air holes play a role in allowing the liquid in the fluid loop 101 to move smoothly through the centrifugal force. For example, these air holes can be formed with a groove formed on the first substrate and a penetrating opening in communication with the groove formed on the second substrate or binding seal strip stacked on the first substrate. In order to prevent the liquid from leaking from the air holes, these air holes are disposed at a side (a side upstream of the centrifugal force direction) closer to a central portion of the assay chip than the connected groove.

The first groove 10, the second groove 20 and the third groove 30 respectively have injection portions (not shown) used for injecting the first liquid, the second liquid, and the third liquid. These injection portions are penetrating openings penetrating along the thickness direction and formed on the second substrate or binding seal strip stacked on the first substrate. Additionally, these penetrating openings can also function as an air hole.

Figure 1:
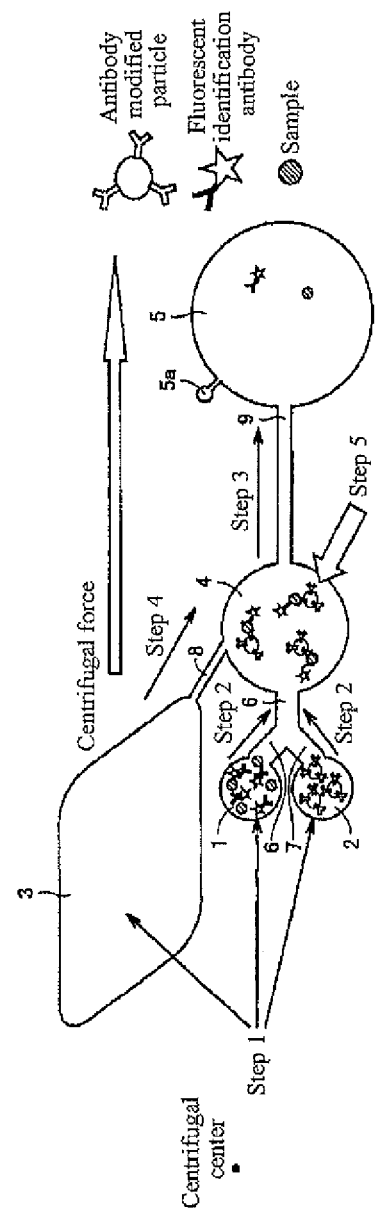
FIG. 1 is a schematic top view showing a constitution of a fluid loop of an assay chip which can clean and remove an unreacted substance.

The cross-sectional areas of the first flow path to the fourth flow path are designed in a manner of the first flow path 14=(or ≈) the second flow path 24>the fourth flow path 45>the third flow path 34, which is the same as the fluid loop shown in FIG. 1. The cross-sectional areas of the first flow path 14 and the second flow path 24 can be set to a value such as about 600×600 to 900×900 μm'. The cross-sectional area of the third flow path 34 can be set to a value such as about 100×20 to 200×50 μm², and the cross-sectional area of the fourth flow path 45 can be set to a value such as about 80×50 to 200×50 μm². In a case where the antibody decorated particle is used to implement a detection method such as the immunofluorescent antibody method, in order to prevent the antibody decorated particle from leaking to the fifth groove 50, the cross-sectional area of the fourth flow path 45 is less than the size of the antibody decorated particle.

In addition to including the first buffering groove 60, the fluid loop 101 of the present embodiment further includes a second buffering groove 70. The second buffering groove 70 is connected to the third groove 30 and the fourth groove 40 through flow paths (respectively, the fifth flow path 37, and the sixth flow path 47), so a path from the third groove 30 to the fourth groove 40 is formed, which is different from a path from the third groove 30 through the third flow path 34 to the fourth groove 40. Referring to FIG. 3, the location of connection of the third flow path 34 and the fourth groove 40 is on the right side of the fourth groove 40, while the location of connection of the sixth flow path 47 and the fourth groove 40 is on the left side of the fourth groove 40 (a side opposite to the location of connection of the third flow path 34 and the fourth groove 40). The second buffering groove 70 is disposed at a side closer to the peripheral portion of the assay chip than the third groove 30 (a side downstream of the centrifugal force direction), and at a side closer to the central portion of the assay chip than the fourth groove 40 (a side upstream of the centrifugal force direction).

According to the fluid loop 101 of the present embodiment further including the second buffering groove 70, the fifth flow path 37 and the sixth flow path 47, when the cleaning fluid in the third groove 30 is guided into the fourth groove 40 to clean the object to be cleaned existing in the fourth groove 40, the cleaning fluid can be guided into the fourth groove 40 from both the left and the right, thereby enhancing cleaning efficiency. However, the second buffering groove 70, the fifth flow path 37 and the sixth flow path 47 are not necessary, but disposed only to accommodate a higher standard of purity.

The size, shape, and cross-sectional area of each groove are appropriately designed according to the quantity of the liquid to be guided into the fluid loop; generally, the cross-sectional area of each groove is sufficiently large relative to the cross-sectional area of the flow path connected between grooves. In the fluid loop 101 of the present embodiment, the fourth groove 40 has an area protruding toward a side of the peripheral portion of the assay chip (a side downstream of the centrifugal force direction) to accommodate an object to be cleaned (a combination containing the antibody decorated particle) during application of the centrifugal force (an object to be cleaned accommodating area), and by collecting the object to be cleaned in the area, the cleaning can be effectively performed (as shown in the drawing, all of the cleaning fluid guided into the fourth groove 40 passes through the area and is discharged to the fifth groove 50).

One of the characteristics of the fluid loop 101 of the present embodiment lies in that the first buffering groove 60 (located between the third groove 30 and the fourth groove 40) is configured on the third flow path 34 connecting the third groove 30 and the fourth groove 40 such that the third liquid accommodated in the third groove 30 can be guided into the fourth groove 40 more than once. The purpose of this configuration is so that when the first buffering groove 60 having the first air hole 61 is inserted, during application of a centrifugal force of a specified magnitude, the third liquid accommodated in the third groove 30 is continuously guided into the fourth groove 40 through the first buffering groove 60. In this case, the third liquid for delivering is in a state of being partially cut off by the first buffering groove 60, or being cut off easily. If the application of the centrifugal force is stopped, the third liquid is cut off in the area where the first air hole 61 exists as a boundary. This cut-off causes a part of the third liquid to be remained in the third groove 30, and the liquid in the third groove 30 and the liquid in the first buffering groove 60 are stopped from flowing.

When a centrifugal force is applied again after the first buffering groove 60 cuts off the third liquid, the first air hole 61 of the first buffering groove 60 functions to allow the third liquid to easily flow (if there were no such hole in the first buffering groove 60, the air in the first buffering groove 60 would expand, thereby restricting the flow of the third liquid).

In a case in which there is no first buffering groove 60, in contrast, the following state occurs: after a centrifugal force with a specified magnitude is applied to guide a part of the third liquid into the fourth groove 40, the third liquid will not be cut off and thereby fully filling the third flow path 34 while the application of the centrifugal force is stopped; when the centrifugal force is applied again, the third liquid flows at a rotation speed less than a specified rotation speed, and finally the liquid in the third groove 30 becomes easy to flow, thereby causing the third liquid in the third groove 30 cannot be divided into many times, and then is guided into the fourth groove 40.

Moreover, for the same reason as described above, in a case in which the second buffering groove 70 is disposed, an air hole is preferably also disposed in the second buffering groove.

FIG. 4 is a schematic view showing experimental results of guiding water in a third groove 30 into a fourth groove 40 more than once by use of a disc-like assay chip of the present invention having the fluid loop 101 shown in FIG. 3. FIG. 4 (*a*) shows a state occurring before a centrifugal force is applied, in which all water is accommodated in the third groove 30. FIG. 4 (*b*) to FIG. 4 (*j*) respectively show states occurring when the application of the centrifugal force is stopped after the centrifugal force is sequentially applied at the first time, the second time . . . , and the ninth time. As shown in FIG. 4, it is proved that each time the centrifugal force is applied (the centrifugal force is applied 9 times in total), a part of the water existing in the third groove 30 (not all) is guided into the fourth groove 40 (moreover, the water guided into the fourth groove 40 reaches the fifth groove 50 through the fourth flow path 45). That is to say, it is proved that according to the disc-like assay chip of the present embodiment, the liquid existing in the third groove can be guided into the fourth groove through segmentation (multi-stage cleaning can be performed on the object to be cleaned existing in the fourth groove). Moreover, presuming no difference in rotation speeds of the assay chip, the less water that remains in the third groove 30, the less centrifugal force is applied to the water, and the more difficult it becomes for the water to be discharged from the third groove 30; so as the process proceeds from FIG. 4 (*b*) to FIG. 4 (*j*), the rotation speed of the assay chip during the application of the centrifugal force is increased.

If a case of performing detection through the immunofluorescent antibody method can be illustrated as an example, the disc-like assay chip of the present embodiment can be used in a manner such as the following. First, a liquid (such as, 5 μL) containing the sample liquid including the target substance and the fluorescent identification antibody is injected in the first groove 10, a liquid (such as, 5 μL) containing the antibody decorated particle is injected in the second groove 20, and a cleaning fluid (such as, 80 μL) is injected in the third groove 30 (step 1). Next, through the rotation of the assay chip whose center serves as the rotation center, a first centrifugal force in the direction shown in FIG. 3 is applied to the assay chip (a centrifugal force which prevents the cleaning fluid from being discharged from the third groove 3), so the liquid containing the sample including the target substance, and the fluorescent identification antibody, and the liquid containing the antibody decorated particle are guided into the fourth groove 40, and these substances are mixed to perform the antigen antibody reaction (step 2).

Then, a second centrifugal force (which is greater than the first centrifugal force) in the direction shown in FIG. 3 is applied, so that the liquid is moved from the fourth groove 40 to the fifth groove 50, thereby moving the waste liquid (step 3).

Next, a third centrifugal force (which is greater than the second centrifugal force) in the direction shown in FIG. 3 is applied. A part of the cleaning fluid in the third groove 30 is guided into the fourth groove 40 to clean the combination of the target substance, the antibody decorated particle and the fluorescent identification antibody, and the cleaning fluid is moved to the fifth groove 50 after the cleaning (step 4). Then, as shown in FIG. 4, step 4 is performed more than once so as to perform multi-stage cleaning. Performing step 4 more than once effectively removes the unreacted sample and the unreacted fluorescent identification antibody. Finally, the detection light is irradiated on the combination of the target substance, the antibody decorated particle and the fluorescent identification antibody accommodated in the fourth groove 40 to perform fluorescent measurement, thereby quantifying the target substance (step 5).

In addition to using the liquid (5 μL) containing the fluorescent identification antibody as the liquid (the first liquid) guided into the first groove 10, using the liquid (5 μL) containing a particle (particle size of 75 μm) not decorated with the antibody as the liquid (the second liquid) guided into the second groove 20, and using the cleaning fluid (Phosphate Buffer Solution (PBS), 80 μL) as the liquid (the third liquid) guided into the third groove 30, step 1 to step 5 are implemented (the cleaning times is about 10 times) in the same manner as described above, and a detection light is irradiated on the object to be cleaned accommodating area; so after fluorescent measurement is performed, the fluorescence intensity is equal to blank (herein, the term "blank" refers to a state in which the cleaning has been proven fully performed). It can be confirmed through the above result that the disc-like assay chip of the present embodiment performs extremely thorough cleaning.

Figure 5:
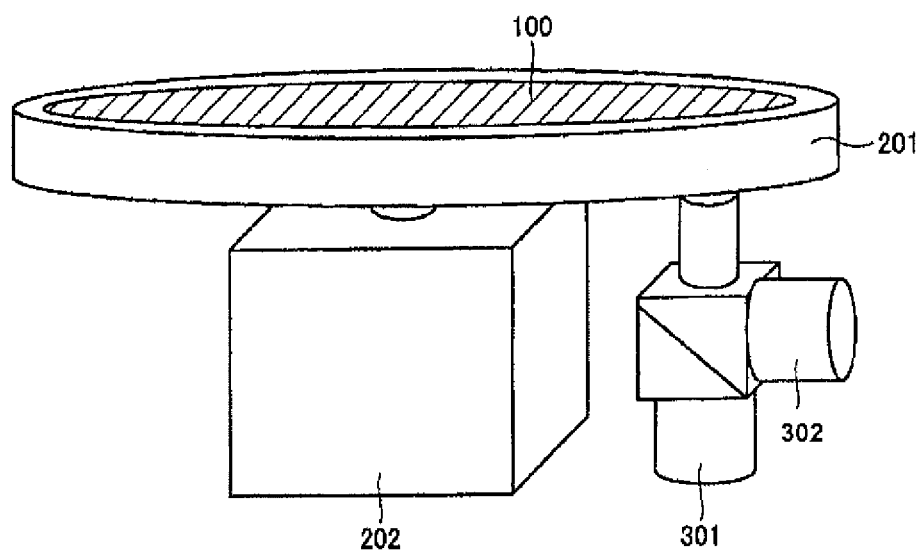
FIG. 5 is a schematic view showing a rotational device used for rotating the disc-like assay chip and a device used for performing optical measurement.
Figure 6:
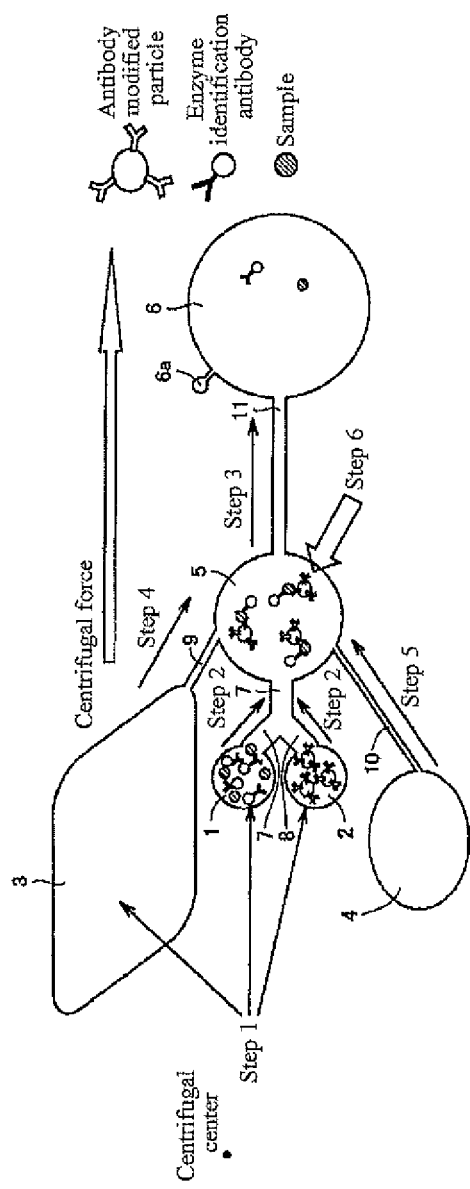
FIG. 6 is a schematic top view showing a constitution of a fluid loop of an assay chip which can implement an ELISA method.

Alternatively, the rotation of the assay chip and optical measurement such as fluorescent measurement can be performed by using a device shown in FIG. 5. The rotational device shown in FIG. 5 includes a rotational disc 201 and a motor 202 used for rotating the rotational disc 201. The disc-like assay chip 100 is mounted on the rotational disc 201, and the rotational disc 201 is rotated by the motor 202 so that the centrifugal force can be provided in the direction of the peripheral portion of the assay chip. The magnitude of the centrifugal force is controlled by the rotation speed of the rotational disc 201.

Additionally, the optical measurement device shown in FIG. 5 includes: a light source 301, used for irradiating a detection light on a specified location (the fourth groove 40 in the present embodiment) of the fluid loop; and a light detector 302, used for detecting fluorescence emitted from a fluorescent substance. As the light source 301, a Light Emitting Diode (LED) and a Laser Diode (LD) can be used, and as the light detector 302, a Photodiode (PD), an Avalanche Photodiode (APD), and a Photomultiplier (PM) can be used.

Figure 7:
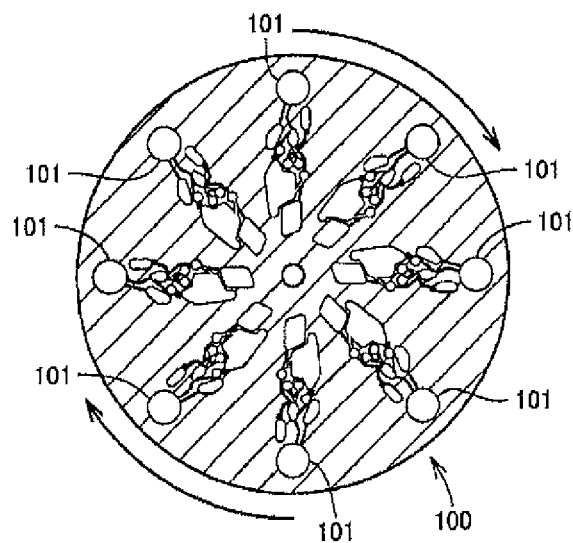
FIG. 7 is a schematic top view showing an example of a disc-like assay chip of the present invention.

FIG. 7 is a schematic top view showing an example of a disc-like assay chip of the present invention. The disc-like assay chip 100 shown in FIG. 7 has fluid loops 101 mainly including various grooves (liquid storage grooves) or minute flow paths connected to these grooves. A centrifugal force is provided by rotating the assay chip along the direction as shown in the drawing (or an opposite direction), and liquids (such as, a sample liquid, a reagent liquid, a cleaning fluid, and a waste liquid) in the fluid loop 101 can be moved to a desired position (location) in the fluid loop 101. In the example shown in FIG. 7, the disc-like assay chip 100 has eight fluid loops 101 of the same shape (pattern), and can simultaneously implement eight detections and assays in parallel. The eight fluid loops 101 are arranged along the radial direction of the disc (that is to say, the direction of the centrifugal force for rotating the assay chip with the center of the disc as the centrifugal center). Moreover, although in the example shown in FIG. 7, the number of fluid loops 101 is eight, but is not limited thereto, or can also be less than or greater than eight.

The fluid loop 101 is a space formed in the disc-like assay chip 100. The disc-like assay chip having this fluid loop can be manufactured by forming a groove pattern corresponding to the constitution of the fluid loop on a disc-like first substrate, and stacking and bonding a second substrate on the groove forming face of the first substrate. The groove pattern forming the fluid loop can also be formed on the stacked second substrate. Additionally, the second substrate can also be replaced, and the disc-like assay chip can be manufactured by stacking other stacking members such as a binding seal strip on the groove forming face of the first substrate.

The substrate material forming the disc-like assay chip is not specially limited, and for example, Polymethyl Methacrylate (PMMA), Polydimethylsiloxane (PDMS), glass, Cyclo Olefin Polymer (COP), Cyclo Olefin Copolymer (COC), Polyethylene Terephthalate (PET), Polystyrene (PS), and Polypropylene (PP) can be employed. For efficiency of production, it is preferable to use PMMA, PET, COP, and COC. In a case where fluorescent measurement is performed while assaying the disc-like assay chip, the substrate material preferably is one that generates fluorescence with difficulty. The material generating fluorescence difficultly preferably is methacrylic resin or cyclo olefin resin, and specifically PMMA, COP, and COC can be used.

The thickness of the disc-like assay chip is not specially limited, and preferably is 0.1 to 100 mm, and more preferably is 2 to 3 mm. The method for forming a groove pattern on a substrate of the disc-like assay chip is not specially limited, and can include a mechanical process, sandblast process, or injection molding. Methods for bonding substrates with each other include melting and welding a binding face of at least one substrate (welding method), and performing adhering by using an adhesive. The welding method can include heating and welding a substrate, performing welding through heat generated during light absorption after a light such as laser light is irradiated (laser welding), or performing welding by using an ultrasonic wave. Preferably, the laser welding method is used.

Figure 8:
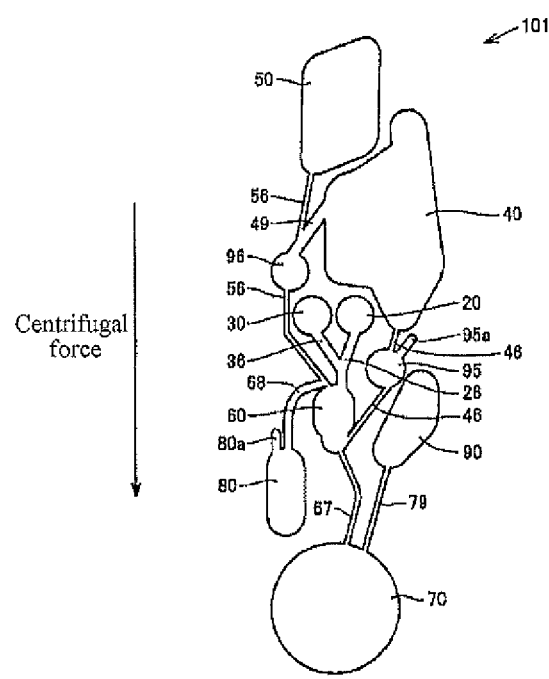
FIG. 8 is a schematic top view showing a preferable example of a constitution of a fluid loop of a disc-like assay chip of the present invention.

Next, an embodiment is illustrated showing the constitution of the fluid loop of the disc-like assay chip of the present invention. FIG. 8 is a schematic top view showing a preferable example of a constitution of a fluid loop of a disc-like assay chip of the present invention, and is an enlarged view showing the fluid loop 101 of the disc-like assay chip 100 shown in FIG. 7. The fluid loop 101 of the disc-like assay chip according to the present embodiment has a constitution as follows, which can be preferably applied to a detection method using the enzymatic reaction such as the ELISA method using the enzyme identification antibody.

As shown in FIG. 8, the fluid loop 101 includes: a first groove 20, used for accommodating a first liquid; a second groove 30, used for accommodating a second liquid; a third groove 40, used for accommodating a third liquid; a fourth groove 50, used for accommodating a fourth liquid; a fifth groove 60, disposed at a side closer to a peripheral portion of the assay chip than the first groove 20, the second groove 30, the third groove 40 and the fourth groove 50; a sixth groove 70, disposed at a side closer to the peripheral portion of the assay chip than the fifth groove 60; a first flow path 26, for connecting the first groove 1 and the fifth groove 60; a second flow path 36, for connecting the second groove 30 and the fifth groove 60; a third flow path 46, for connecting the third groove 3 and the fifth groove 60; a fourth flow path 56, for connecting the fourth groove 4 and the fifth groove 60; and a fifth flow path 67, for connecting the fifth groove 5 and the sixth groove 70.

The sixth groove 70 is connected to a first air hole 90 in communication with the exterior of the assay chip through a seventh flow path 79. The first air hole 90 is disposed at a side closer to the central portion of the assay chip than the sixth groove 70.

Additionally, the fluid loop 101 includes a seventh groove 80, which is disposed at a side closer to the peripheral portion of the assay chip than the fifth groove 60, and is connected to the fifth groove 60 through a sixth flow path 68. The seventh groove 80 has a third air hole 80a in communication with the exterior of the assay chip. The sixth flow path 68 is connected to an upper portion of the fifth groove 60 (the direction of the central portion of the assay chip is set as the upper direction).

Further, the fluid loop 101 includes a first buffering groove 95 configured on the third flow path 46 and having a second air hole 95a in communication with the exterior of the assay chip and a second buffering groove 96. The first buffering groove 95 and the second buffering groove 96 are disposed at a side closer to the central portion of the assay chip than the fifth groove 60. The second buffering groove 96 is connected to the third groove 40 through an eighth flow path 49, and connected to the fifth groove 60 through the fourth flow path 56.

The first air hole 90, the second air hole 95a and the third air hole 80a serve to allow the liquid in the fluid loop 101 to move smoothly due to the application of centrifugal force. For example, these air holes can be formed in a groove formed on the first substrate, and a penetrating opening in communication with the groove can be formed on the second substrate or binding seal strip stacked on the first substrate. In order to prevent the liquid from leaking from the air holes, these air holes are disposed at a side (a side upstream of the centrifugal force direction) closer to a central portion of the assay chip than the connected groove.

The first groove 20, the second groove 30, the third groove 40 and the fourth groove 50 respectively have injection portions (not shown) used for injecting the first liquid, the second liquid, the third liquid and the fourth liquid. These injection portions are penetrating openings penetrating along the thickness direction and formed on the second substrate or binding seal strip stacked on the first substrate. Additionally, these penetrating openings can also play the role of the air hole.

For example, in a case where the disc-like assay chip of the present embodiment is used to perform detection through the ELISA method, the first liquid contains a sample including the target substance as an assay object and an antibody identified with an enzyme (the enzyme identification antibody), the second liquid contains a particle decorated with an antibody (the antibody decorated particle), the third liquid can be a cleaning fluid and the fourth liquid can be a matrix solution. The particle size of the antibody decorated particle is not specially limited; for example, the commonly employed antibody decorated particle size of 75 µm can be used.

Herein, in the disc-like assay chip of the present embodiment, the cross-sectional areas of the first flow path to the fifth flow path are designed in a manner such that the first flow path 26=(or ≈) the second flow path 36>the fifth flow path 67>the third flow path 46>the fourth flow path 56. The width and the depth of each flow path are not specially limited as long as they satisfy the relationship of the cross-sectional area; for example, the width and the depth can have a range of several µm or dozens of µm to hundreds of µm (or to the extent of thousands of µm). In a case where the antibody decorated particle is used to implement a detection method such as the ELISA method, in order to prevent the antibody decorated particle from leaking to the sixth groove 70, the cross-sectional area of the fifth flow path 67 is less than the size of the antibody decorated particle.

Additionally, in the disc-like assay chip of the present embodiment, the total volume of the fifth flow path 67 and the sixth groove 70 are designed to be less than the total volume of the first liquid, the second liquid, the third liquid and the fourth liquid.

According to the disc-like assay chip of the present embodiment having the fluid loop 101 of the constitution as described above, in the step of guiding the fourth liquid in the fourth groove 50 into the fifth groove 60, the fourth liquid can be deposited in the fifth groove 60. Therefore, in a case where, for example, the ELISA method is implemented, the enzymatic reaction through the fourth liquid (the matrix solution) can be fully performed, thereby improving detection precision.

Illustrated below is an embodiment in which the disc-like assay chip is employed to perform detection through the ELISA method.

First, the liquid (the first liquid) containing the sample including the target substance and the enzyme identification antibody is injected in the first groove 20, the liquid (the second liquid) containing the antibody decorated particle is injected in the second groove 30, the cleaning fluid (the third liquid) is injected in the third groove 40, and the matrix solution (the fourth liquid) is injected in the fourth groove 50 (step 1). Next, through the rotation of the assay chip whose center serves as the rotation center, a first centrifugal force in the direction shown in FIG. 8 is applied to the assay chip (a centrifugal force which prevents the cleaning fluid from being discharged from the third groove 40 and prevents the matrix solution from being discharged from the fourth groove 50), so the liquid (the first liquid) containing the sample including the target substance and the enzyme identification antibody, and the liquid (the second liquid) containing the antibody decorated particle are guided into the fifth groove 60 and these substances are mixed to perform the antigen antibody reaction (step 2).

Then, a second centrifugal force (which is greater than the first centrifugal force) in the direction shown in FIG. 8 is applied, so that the liquid is moved from the fifth groove 60 to the sixth groove 70, thereby moving the waste liquid (step 3).

Next, a third centrifugal force (which is greater than the second centrifugal force and sufficient to prevent the matrix solution from being discharged from the fourth groove 50) in the direction shown in FIG. 8 is applied, a part of the cleaning fluid (the third liquid) in the third groove 40 is guided into the fifth groove 60 to clean the combination of the target substance, the antibody decorated particle and the enzyme identification antibody, and the cleaning fluid is moved to the sixth groove 70 after the cleaning (step 4). Then, step 4 is performed more than once to perform multi-stage cleaning. By performing step 4 more than once, the unreacted sample and the unreacted enzyme identification antibody are effectively removed. Moreover, as described below, this multi-stage cleaning performed by guiding the cleaning fluid into the third groove 40 through dividing is achieved by disposing the first buffering groove 95 and/or the second buffering groove 96.

Figure 9A:
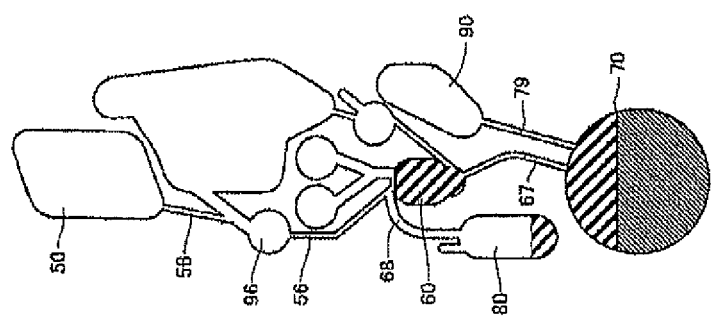
FIGS. 9 (a) and 9 (b) are schematic views showing states of a liquid in several steps of using the disc-like assay chip of the present invention having the fluid loop shown in FIG. 8 to implement the ELISA method.
Figure 9B:
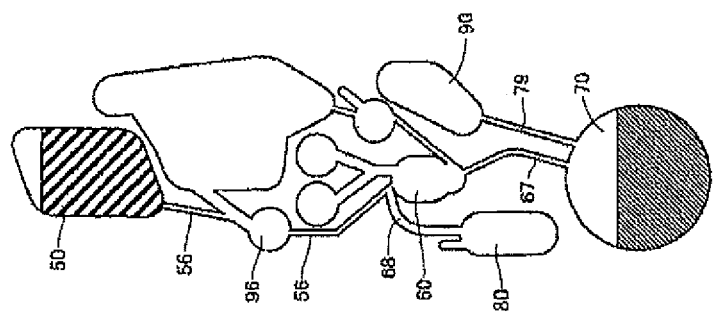

FIG. 9 (a) shows the liquid in the fluid loop 101 in a state in which the step 4 is performed more than once. As shown in the drawing, the first liquid to the third liquid (except the combination containing the antibody decorated particle) in the stage are accommodated in the sixth groove 70, and the fourth liquid, that is, the matrix solution, is maintained in the fourth groove 50.

Next, a fourth centrifugal force (which is greater than the third centrifugal force) in the direction shown in FIG. 8 is applied, and the matrix solution (the fourth liquid) in the fourth groove 50 is guided into the fifth groove 60 to perform the enzymatic reaction (step 5). In this case, as described above, the total volume of the fifth flow path 67 and the sixth groove 70 is less than the total volume of the first liquid to the fourth liquid, so the matrix solution cannot be completely accommodated in the fifth flow path 67 and the sixth groove 70; then, the matrix solution is deposited in the fifth groove 60 (referring to FIG. 9 (b)) to perform the enzymatic reaction. In the example shown in FIG. 9 (b), the total volume of the fifth flow path 67 and the sixth groove 70 is sufficiently small that the fifth groove 60 becomes completely filled with the matrix solution and the redundant matrix solution overflows into the seventh groove 80.

Finally, the fluorescent substance generated in the fifth groove 60 is detected through the enzymatic reaction (the detection light is irradiated on the fifth groove 60), thereby quantifying the target substance (step 6).

As described above, according to the disc-like assay chip of the present embodiment, in the step of guiding the matrix solution (the fourth liquid) into the fifth groove 60, the matrix solution can be deposited in the fifth groove 60 to allow more complete enzymatic reaction through the matrix solution, thereby enhancing the precision of detection achieved by the ELISA method.

As long as the total volume of the fifth flow path 67 and the sixth groove 70 is less than the total volume of the first liquid to the fourth liquid, the size, the shape, and the cross-sectional area of each groove are not specially limited, and are appropriately set according to the quantity of the liquid guided into the fluid loop 101; generally, the cross-sectional area of each groove is sufficiently larger than the cross-sectional area of a flow path connected between grooves. In the fluid loop 101 of the present embodiment, the fifth groove 60 has an area protruding to a side of the peripheral portion of the assay chip (a side downstream of the centrifugal force direction) for accommodating an object to be cleaned (a combination containing the antibody decorated particle) during application of centrifugal force; by collecting the object to be cleaned in this area, the cleaning can be effectively performed (it can be understood according to FIG. 8 that all of the cleaning fluid guided into the fifth groove 60 passes through the area and is discharged to the sixth groove 70).

The volume of the sixth groove 70 preferably is greater than the total volume of the first liquid to the third liquid (except the combination containing the antibody decorated particle), and is less than the total volume of the first liquid to the fourth liquid (except the combination containing the antibody decorated particle).

The total volume of the fifth groove 60, the fifth flow path 67 and the sixth groove 70 can also be less than the total volume of the first liquid to the fourth liquid. In this case, preferably the seventh groove 80 is used, and the seventh groove 80 accommodates the fourth liquid overflowing from the fifth groove 60 when the fourth liquid (the matrix solution) is guided in step 5. However, the total volume of the fifth groove 60, the fifth flow path 67 and the sixth groove 70 can be designed to be greater the total volume of than the first liquid to the fourth liquid, and the seventh groove 80 and the sixth flow path 68 can be omitted.

When the fourth liquid (the matrix solution) is guided in step 5, preferably the cross-sectional area of the fifth flow path 67 is set to be the same or substantially the same as the cross-sectional area of the seventh flow path 79, so that the fourth liquid can be more reliably deposited in the fifth groove 60. In a case where the cross-sectional area of the seventh flow path 79 is larger than that of the fifth flow path 67, there is a tendency for the fourth liquid to easily leak from the first air hole 90 instead of being deposited in the fifth groove 60.

Next, the first buffering groove 95 and the second buffering groove 96 are illustrated. In the present invention, these buffering grooves are randomly disposed. The first buffering groove 95 has the second air hole 95a, and is configured on the third flow path 46 connecting the third groove 40 and the fifth groove 60. By employing the first buffering groove 95, the third liquid (the cleaning fluid) accommodated in the third groove 40 can be guided into the fifth groove 60 more than once.

In the case where the first buffering groove 95 has the second air hole 95a, during application of a centrifugal force of a specified magnitude, the third liquid accommodated in the third groove 40 is continuously guided into the fifth groove 60 through the first buffering groove 95. In this case, the third liquid for delivering is in a state of being partially cut off by the first buffering groove 95, or being cut off easily. If the application of centrifugal force is stopped, the third liquid is cut off in the area where the second air hole 95a exists as a boundary. This cut-off causes a part of the third liquid to be left in the third groove 40, and the liquid in the third groove 40 and the liquid in the first buffering groove 95 are stopped from flowing.

When a centrifugal force is applied again after the first buffering groove 95 cuts off the third liquid, the second air hole 95a of the first buffering groove 95 functions to allow the third liquid to easily flow (if there were no such air hole in the first buffering groove 95, the air in the first buffering groove 60 would expand, thereby restricting the flow of the third liquid).

In a case in which there is no first buffering groove 95, in contrast, the following state occurs: after a centrifugal force with a specified magnitude is applied to guide a part of the third liquid into the fifth groove 60, the third liquid will not be cut off and thereby fully filling the third flow path 46 while the application of the centrifugal force is stopped; when the centrifugal force is applied again, the third liquid flows at a rotation speed less than a specified rotation speed, and finally the liquid in the third groove 40 becomes easy to flow, thereby causing the third liquid in the third groove 40 cannot be divided into many times, and then is guided into the fifth groove 60.

In this way, by employing the first buffering groove 95, the third liquid in the third groove 40 can be guided into the fifth groove 60 more than once; that is to say, the object to be cleaned in the fifth groove 60 can be cleaned more than once. Thereby, the cleaning effect in step 4 can be significantly improved. This improvement in cleaning effect greatly enhances the precision of detection.

In addition to the first buffering groove 95, the second buffering groove 96 can also be disposed. The second buffering groove 96 is connected to the third groove 40 and the fifth groove 60 through flow paths (respectively, the eighth flow path 49 and the fourth flow path 56), so a path from the third groove 40 to the fifth groove 60 is formed, which is different from a path from the third groove 40 through the third flow path 46 to the fifth groove 60. Referring to FIG. 8, the location of connection of the third flow path 46 and the fifth groove 60 is the right side of the fifth groove 60, whereas the location of connection of the fourth flow path 56 and the fifth groove 60 is the left side of the fifth groove 60.

In a case where the second buffering groove 96 and the eighth flow path 49 are further included, when the cleaning fluid in the third groove 40 is guided into the fifth groove 60 to clean the object to be cleaned existing in the fifth groove 60, the cleaning fluid can be guided into the fifth groove 60 from both the left and the right, so as to further improve the cleaning effect. Moreover, according to the same reason as described above, in a case where the second buffering groove 96 is employed, an air hole can also be disposed in the second buffering groove 96.

As described above, the first buffering groove 95 and the second buffering groove 96 are disposed as required according to the desired level of purity.

Moreover, the rotation of the assay chip and the optical measurement as shown in step 6 can be performed by using the device shown in FIG. 5.

While several embodiments of the present invention have been illustrated and described, various modifications and improvements can be made by those skilled in the art. The embodiments of the present invention are therefore described in an illustrative but not in a restrictive sense. It is intended that the present invention should not be limited to the particular forms as illustrated and that all modifications which maintain the spirit and scope of the present invention are within the scope defined in the appended claims.

What is claimed is:

1. A disc-like assay chip, comprising an internal space, wherein a centrifugal force is applied to move a liquid existing in the internal space to a desired position in the internal space, and
the internal space comprises:
a first groove, used for accommodating a first liquid;
a second groove, used for accommodating a second liquid;
a third groove, used for accommodating a third liquid;
a fourth groove, used for accommodating a fourth liquid;
a fifth groove, disposed at a side closer to a peripheral portion of the assay chip than the first groove, the second groove, the third groove and the fourth groove;
a sixth groove, disposed at a side closer to the peripheral portion of the assay chip than the fifth groove;
a first flow path, for connecting the first groove and the fifth groove;
a second flow path, for connecting the second groove and the fifth groove;
a third flow path, for connecting the third groove and the fifth groove;
a fourth flow path, for connecting the fourth groove and the fifth groove; and
a fifth flow path, for connecting the fifth groove and the sixth groove;
wherein a transversal cross-sectional area of the first flow path and that of the second flow path are greater than that of a transversal cross-sectional area fifth flow path, a transversal cross-sectional area of the fifth flow path is greater than that of the third flow path, and a transversal cross-sectional area of the third flow path is greater than that of the fourth flow path.

2. The disc-like assay chip according to claim 1, further comprising a seventh groove, which is disposed at a side closer to the peripheral portion of the assay chip than the fifth groove, and is connected to the fifth groove through a sixth flow path.

3. The disc-like assay chip according to claim 1, further comprising a first air hole, which is disposed at a side closer to a central portion of the assay chip than the sixth groove, is connected to the sixth groove through a seventh flow path, and is in communication with an exterior of the assay chip.

4. The disc-like assay chip according to claim 2, further comprising a first air hole, which is disposed at a side closer to a central portion of the assay chip than the sixth groove, is connected to the sixth groove through a seventh flow path, and is in communication with an exterior of the assay chip.

5. The disc-like assay chip according to claim 3, wherein the cross-sectional area of the fifth flow path and the transversal cross-sectional area of the seventh flow path are substantially the same.

6. The disc-like assay chip according to claim 4, wherein the transversal cross-sectional area of the fifth flow path and the transversal cross-sectional area of the seventh flow path are substantially the same.

7. The disc-like assay chip according to claim 1, further comprising a first buffering groove positioned along the third flow path, and having a second air hole in communication with an exterior of the assay chip.

8. The disc-like assay chip according to claim 2, further comprising a first buffering groove positioned along the third flow path, and having a second air hole in communication with an exterior of the assay chip.

9. The disc-like assay chip according to claim 7, further comprising a second buffering groove, which is disposed at a side closer to a central portion of the assay chip than the fifth groove, and is connected to the third groove and the fifth groove through a flow path.

10. The disc-like assay chip according to claim 8, further comprising a second buffering groove, which is disposed at a side closer to a central portion of the assay chip than the fifth groove, and is connected to the third groove and the fifth groove through a flow path.

11. A method of operating a disc-like assay chip as in claim 1, comprising:
applying the first liquid in the first groove, the first liquid comprising a sample as an assay object and an antibody identified with an enzyme;
applying the second liquid in the second groove, the second liquid comprising a particle decorated with an antibody;
applying the third liquid in the third groove, the third liquid comprising a cleaning fluid;
applying the fourth liquid in the fourth groove, the fourth liquid comprising a matrix solution.

12. A method of operating a disc-like assay chip as in claim 2, comprising:
applying the first liquid in the first groove, the first liquid comprising a sample as an assay object and an antibody identified with an enzyme;
applying the second liquid in the second groove, the second liquid comprising a particle decorated with an antibody;
applying the third liquid in the third groove, the third liquid comprising a cleaning fluid;
applying the fourth liquid in the fourth groove, the fourth liquid comprising a matrix solution.

13. The method of operating a disc-like assay chip as in claim 11, further comprising:
controlling a total volume of the first liquid, the second liquid, the third liquid, and the fourth liquid to be greater than a total volume of the fifth flow path and that of the sixth groove.

14. The method of operating a disc-like assay chip as in claim 11, further comprising:
applying a first centrifugal force which prevents the third liquid from being discharged from the third groove and prevents the fourth liquid from being discharged from the fourth groove, so as to move the first liquid the and second liquid to the fifth groove;
applying a second centrifugal force greater than the first centrifugal force and sufficient to move the first liquid the and second liquid from the fifth groove to the sixth groove;
applying a third centrifugal force greater than the second centrifugal force and sufficient to prevent the fourth liquid from being discharged from the fourth groove so as to move the third liquid from the third groove to the fifth groove, and further to the sixth groove; and
applying a fourth centrifugal force greater than the third centrifugal force and sufficient to move the fourth liquid from the fourth groove to the fifth groove
wherein the third centrifugal force is applied multiple times.

15. The disc-like assay chip according to claim 1, wherein the third groove accommodates cleaning fluid for cleaning the fifth groove.

16. The disc-like assay chip according to claim 7, wherein the first buffering groove and the second air hole are configured to cutoff the third liquid moving from the third groove to the fifth groove when the centrifugal force stops.

17. The disc-like assay chip according to claim 8, wherein the first buffering groove and the second air hole are configured to cutoff the third liquid moving from the third groove to the fifth groove when the centrifugal force stops.

18. The disc-like assay chip according to claim 9, wherein the second buffering groove is configured to move the third liquid in the third groove to the fifth groove when the centrifugal force is applied.

19. The disc-like assay chip according to claim 10, wherein the second buffering groove is configured to move the third liquid in the third groove to the fifth groove when the centrifugal force is applied.

20. The disc-like assay chip according to claim 2, wherein the seventh groove is configured to accommodate overflow liquid from the sixth groove.

21. The disc-like assay chip according to claim 1, wherein the first groove and the second groove are merged to a fifth groove through the first flow path and the second flow path and the first liquid and the second liquid are mixed in the fifth groove.

22. The disc-like assay chip according to claim 1, wherein the fourth groove is configured to transport a matrix solution to the fifth groove through the fourth flow path.

* * * * *